US012667409B2

(12) United States Patent

Helzer et al.

(10) Patent No.: US 12,667,409 B2

(45) Date of Patent: Jun. 30, 2026

(54) SURGICAL INSTRUMENT WITH AN EXTENDABLE LOOP MADE OF METAL WIRE THAT CAN BE ENERGIZED

(71) Applicant: RZ-Medizintechnik GmbH, Tuttlingen (DE)

(72) Inventors: Markus Helzer, Zimmern (DE); Alexander Doppelstein, Spaichingen (DE); Tobias Zubrod, Tuttlingen (DE)

(73) Assignee: RZ-MEDIZINTECHNIK GMBH, Tuttlingen (DE)

( * ) Notice: Subject to any disclaimer, the term of this patent is extended or adjusted under 35 U.S.C. 154(b) by 560 days.

(21) Appl. No.: 18/125,487

(22) Filed: Mar. 23, 2023

(65) Prior Publication Data

US 2023/0301706 A1     Sep. 28, 2023

(30) Foreign Application Priority Data

Mar. 24, 2022    (DE) ..................... 10 2022 107 017.4

(51) Int. Cl.
   *A61B 18/14*        (2006.01)
   *A61B 18/00*        (2006.01)
(52) U.S. Cl.
   CPC .... *A61B 18/14* (2013.01); *A61B 2018/00077* (2013.01); *A61B 2018/00589* (2013.01); *A61B 2018/00601* (2013.01); *A61B 2018/00625* (2013.01); *A61B 2018/00922* (2013.01); *A61B 2018/1407* (2013.01)
(58) Field of Classification Search
   CPC .......... A61B 18/14; A61B 2018/00077; A61B 2018/00589; A61B 2018/00601; A61B
2018/00625; A61B 2018/00922; A61B
2018/1407; A61B 2018/0091; A61B
2018/00916; A61B 2018/00946
   USPC .......................................................... 606/41
See application file for complete search history.

(56) References Cited

U.S. PATENT DOCUMENTS 10,813,685 B2 * 10/2020 Sartor ................ A61B 18/1482

FOREIGN PATENT DOCUMENTS

| DE | 102 12 841 A1 | 10/2003 |
| DE | 10 2017 126 199 A1 | 5/2019 |
| DE | 10 2020 118 965 A1 | 2/2022 |

OTHER PUBLICATIONS

Office Action issued Dec. 8, 2022 in DE 10 2022 107 017.4.

* cited by examiner

*Primary Examiner* — Beverly M Flanagan
(74) *Attorney, Agent, or Firm* — Panitch Schwarze Belisario & Nadel LLP

(57) ABSTRACT

A surgical instrument comprised of a handle and a tubular shaft with an interior and a wall made from an electrically conductive material. A metallic wire is arranged at least in sections in the interior of the tubular shaft and can be moved by the actuation of a control element so that a loop that can be extended out of a distal end of the shaft is formed and with a switch, wherein the metallic wire can be energized by the actuation of the switch, in which the control element and the switch are coupled with each other so that the metallic wire is energized in defined positions of the metallic wire.

8 Claims, 3 Drawing Sheets

SURGICAL INSTRUMENT WITH AN EXTENDABLE LOOP MADE OF METAL WIRE THAT CAN BE ENERGIZED

CROSS-REFERENCE TO RELATED APPLICATIONS

This application claims priority under 35 U.S.C. § 119(b) to German Patent Application No. 10 2022 107 017.4, filed on Mar. 24, 2022, the disclosure of which is incorporated herein by reference in its entirety.

BACKGROUND OF THE INVENTION

The invention relates to a surgical instrument with an extendable loop made of metal wire that can be energized.

Surgical instruments are known with a shaft, which has a longitudinal axis, a proximal end, and a distal end, and with an extendable loop made from a metallic wire. Here, extendable means that the position of at least some sections of the metallic wire within the shaft can be changed, so that, for example, the position of the loop relative to the distal end of the shaft and/or its size can be changed. DE 10 2017 126 199 A1 discloses an example of such a surgical instrument.

In principle, the metallic wire can be energized with current, but it can also be used without current. If the metallic wire is used without current, the surgical instrument can be used, for example, for dilating or dissecting tissue. By energizing the metallic wire with current, the surgical instrument can be used for resecting tissue, for example, of polyps or myomas, for the coagulation of tissue, or for vaporizing tissue. Here, the instrument can be used both in a monopolar and also in a bipolar configuration.

In the practical use of surgical instruments, whose metallic wire can be energized with current, it has been shown that energizing the metallic wire leads to problems in certain positions of the loop. This applies especially to positions, in which the dissipation of heat generated when the metallic wire is energized is not guaranteed, so that there is local overheating of the metallic wire. Such overheating is especially critical in metallic wires made from a shape memory alloy, e.g., nitinol, wherein, during production of the surgical instrument, the section of the metallic wire extended out of the shaft and, in particular, a loop formed by this section, learns a defined shape that it is supposed to assume, because during the overheating, this section learns a new, undefined shape that can then make the intended use of the surgical instrument more difficult or completely impossible.

BRIEF SUMMARY OF THE INVENTION

The task of the invention is to refine a surgical instrument with an extendable loop made from a metallic wire that can be energized such that excessive heating of sections of the metallic wire is avoided with higher reliability.

The task of the invention is solved by a surgical instrument with the features described herein. Advantageous constructions and refinements of the invention are specified in the dependent claims.

The surgical instrument according to the invention has a handle formed preferably by a housing and a tubular shaft with an interior and a wall made from an electrically conductive material. A metallic wire, which can be made preferably from a shape memory alloy, e.g., nitinol, is arranged at least in sections in the interior of the tubular shaft and can be moved by actuating a control element, so that a loop that can be extended out of a distal end of the shaft is formed. The surgical instrument further has a switch, which can energize the metallic wire when it is actuated. Accordingly, the distal end of the surgical instrument is the end at which the loop is arranged; its proximal end is the end opposite the distal end, whereby the proximal and distal directions are uniquely defined with respect to the device.

The extendable loop is here preferably formed such that one end of the metallic wire is fastened in electrically conductive contact at the distal end of the wall made from an electrically conductive material of the tubular shaft; in principle, however, two sections of the metallic wire could also be guided electrically insulated from each other in the interior of the tubular shaft.

Here it is understood that in the radial direction relative to the center axis of the tubular shaft there is electrical insulation for the metallic wire in the sections that might come into contact with the wall made from electrically conductive material.

It is preferred for the invention that the control element and the switch are coupled with each other, so that the metallic wire is energized only in one or more defined positions of the metallic wire. In other words, the control element is used both to produce the mechanical change in position of the metallic wire and also to move the switch into a different switching position. In this way it can be guaranteed that a flow of current and thus heating of the metallic wire can take place only in certain positions of the metallic wire.

Here it is especially preferred if the metallic wire is energized only in the position of the control element, in which the extendable loop is extended as far as possible. In this way it is reliably avoided that sections of the metallic wire that are used for forming the extendable loop are heated by the energization, while they are arranged inside the tubular shaft, which then prevents the dissipation of heat that could produce overheating of the metallic wire, which could have the effect, for example, if the metallic wire is made out of a shape memory alloy that has learned a desired loop shape, that this loop shape could be changed.

It is advantageous if the control element is held in the position, in which the metallic wire is energized, so that a holding force must be overcome to move the control element into a different position. This leads, on one hand, to an intimate electrical contact between the switch contacts of the switch and, on the other hand, ensures that the extendable loop is extended as far as possible.

In addition it can be advantageous if the control element is held in the position, in which the loop is as small as possible or retracted completely into the interior of the tubular shaft, so that a holding force must be overcome to move the control element into a different position. This arrangement counteracts the loop being unintentionally extended and the metallic wire being unintentionally energized.

A holding force like this can be provided in an especially easy way by a spring element.

In one especially preferred embodiment of the invention, the control element is part of a slide, wherein the slide further has a body, in which an end section of the metallic wire is held and fixed. This body is advantageously arranged within the housing so that it can be moved and can be connected, for example, with a connecting section to the control element. In one especially advantageous variant, the connecting section can be guided in a recess of the housing running parallel to the center axis of the tubular shaft, so that the control element can be moved only in the proximal and distal directions, so that the body moves at the same time and the metallic wire held in this body with one end section moves correspondingly within the tubular shaft.

The coupling of the control element with the switch is realized here in an especially simple way with a configuration, in which a bearing section of a contact element, which is connected in an electrically conductive way to the metallic wire, is housed in the body of the slide and in which a contact section of the contact element projects out of the body of the slide, so that the slide forms a control element of the switch and the contact section of the contact element forms a first switching contact of the switch.

In this configuration, it is preferred that a second switching contact of the switch is formed by a distal end section of an electrode that is constructed as a sheet and is preferably the active electrode, which is connected to an electrical connection of the surgical instrument.

If the distance of the distal end section of the electrode constructed as a sheet from a center axis of the tubular shaft then decreases in the distal direction, which can be achieved especially when the distal end section of the electrode constructed as a sheet is kinked or bent from the adjacent section of the electrode constructed as a sheet, and if further the contact section of the contact element has a first contact surface that is essentially parallel to the distal end section of the electrode constructed as a sheet, so that movement of the slide in the distal direction can produce a surface area contact between the first contact surface and the distal end section of the electrode constructed as a sheet and an especially good electrical contact can be guaranteed.

Embodiments are especially preferred in which the contact section of the contact element has a second contact surface, whose distance from the center axis of the tubular shaft decreases in the proximal direction and in which, when the switch is closed and the loop is completely extended, the spring element contacts the second contact surface, and when the slide moves in the proximal direction, the spring element is further tensioned by the second contact surface, because in this way, a holding force that holds the loop in its maximum extended state can be generated in a simple way.

BRIEF DESCRIPTION OF THE SEVERAL VIEWS OF THE DRAWING

The foregoing summary, as well as the following detailed description of the preferred invention, will be better understood when read in conjunction with the appended drawings. 4ot the purpose of illustrating the preferred invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figures 1, 2:
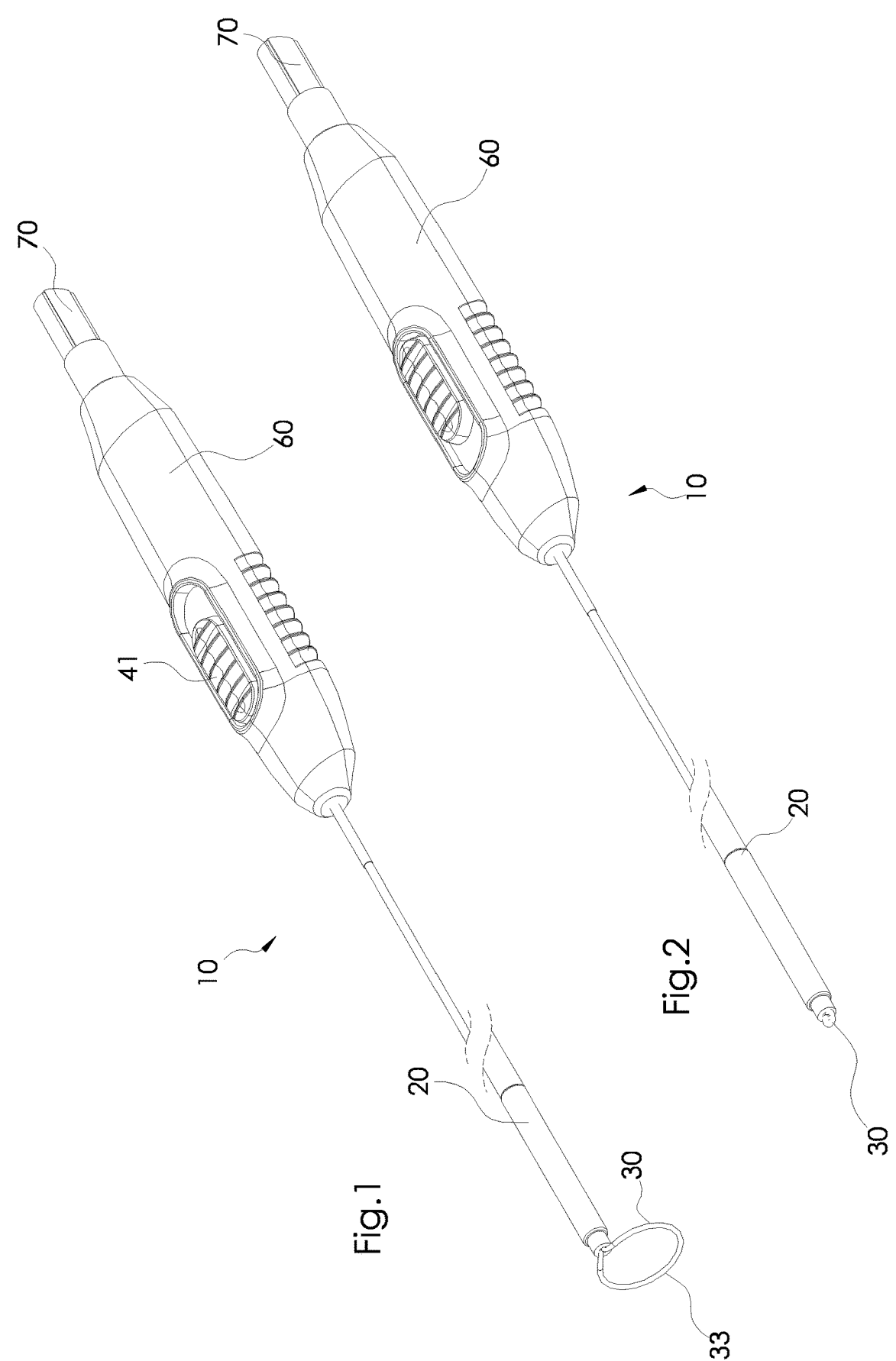
FIG. 1 is a top perspective view of a surgical instrument with an extended loop made from a metallic wire that can be energized.
FIG. 2 is an alternative top perspective view of surgical instrument of FIG. 1 with a retracted loop that can be energized.
Figure 3:
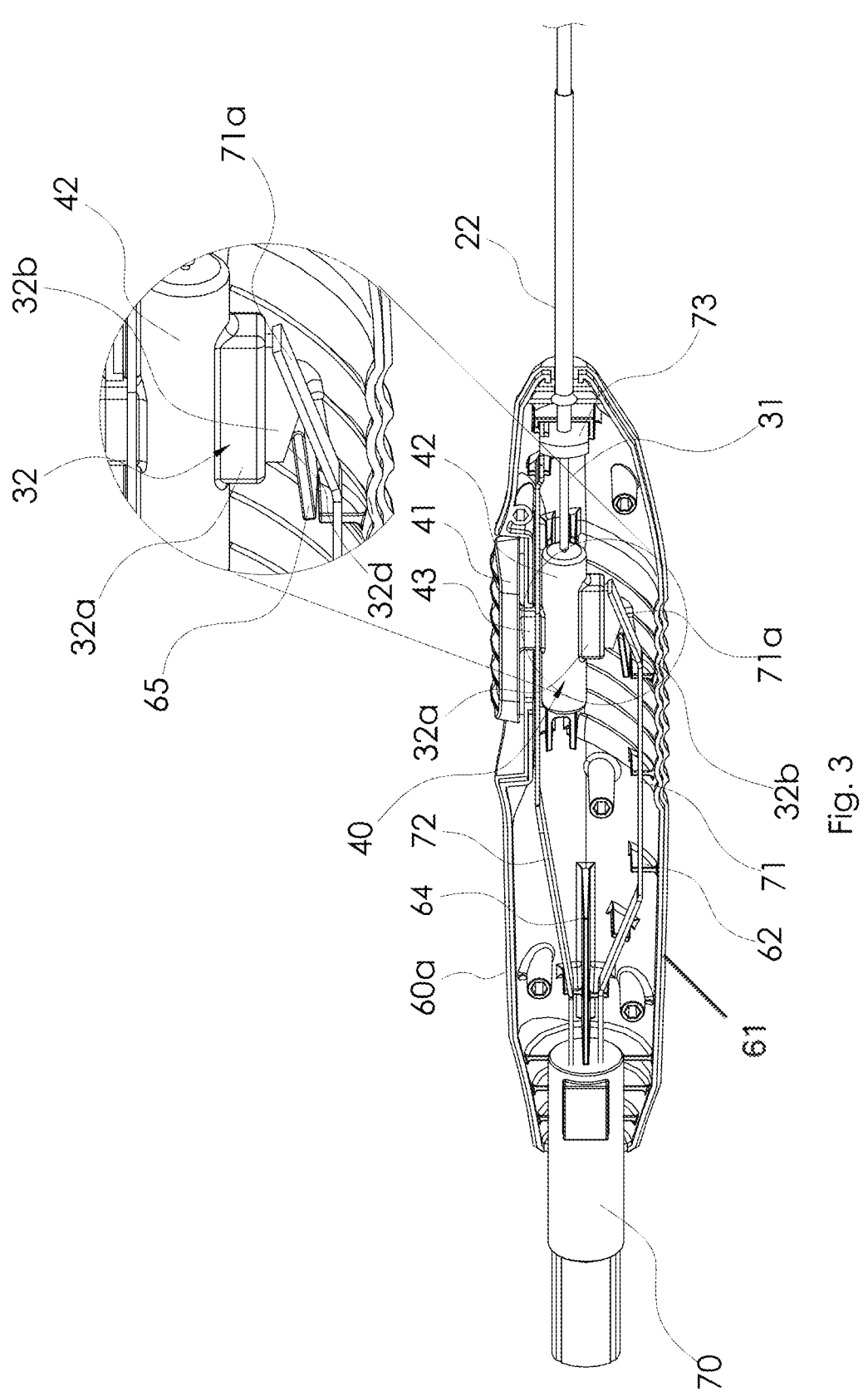
FIG. 3 is a cross-sectional view of the surgical instrument of FIG. 1, taken along a longitudinal axis of the surgical instrument and a magnified view of an interior of a housing of the surgical instrument of FIG. 1.
Figure 4:
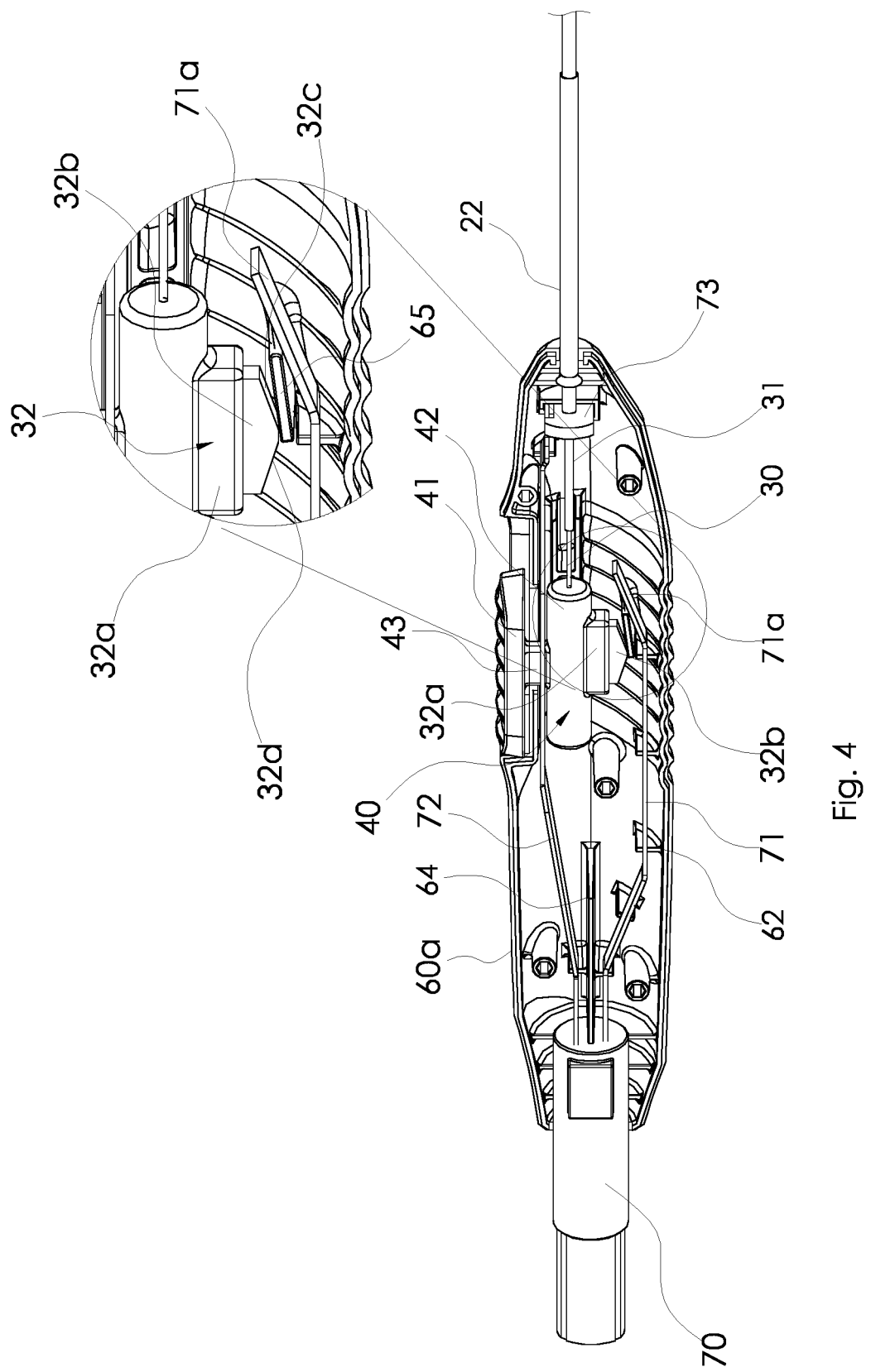
FIG. 4 is an alternative cross-sectional view of the surgical instrument of FIG. 1, taken along a longitudinal axis of the surgical instrument of FIG. 2 and a magnified view of an interior of a housing of the surgical instrument of FIG. 2.

The surgical instruments 10 shown in FIGS. 1 and 2, respectively, has a handle 60 typically formed from a plastic and a tubular shaft 20 with an interior, whose distal end section is shown enlarged in FIGS. 3 and 4.

In the interior of the tubular shaft 20 there is a metallic wire 30, which can be moved at least in sections by actuating a control element 41 constructed as part of a slide 40. In the position of the control element 41 shown in FIG. 1, the metallic wire 30 is extended, so that it forms a loop 33. In the position of the control element 41 that is constructed as a slide and is shown in FIG. 2, the metallic wire 30 is retracted, so that it is arranged almost completely in the interior of the tubular shaft 20.

By means of an electrical connection 70 arranged on the proximal end of the handle 60, the connection to a not shown power source can be established, so that the metallic wire 30 and especially a loop 33, which the wire forms in the extended state, can be energized.

In FIGS. 3 and 4, a concrete way to realize this arrangement is seen. An active electrode 71 and a passive electrode 72, which can each be formed by one-piece, machine-bent, and laser-cut sheets, extend from the electrical connection 70. These sheets can be guided and held especially by guiding elements 62 arranged on the housing wall 61, of which, in the figures, only those for the active electrode 71 are shown as an example, e.g., when the active electrode 71 and the passive electrode 72 are pushed in the guiding elements 62. Here, in the area in which the active electrode 71 and the passive electrode 72 extend from the electrical connection 70, there can be an insulating means in the form of a rib 64 injection molded on the housing wall 61.

The end of the passive electrode 72 can be held in a spring-mounted way in a slot of a flange 73 made from electrically conductive material, in which the proximal end of an electrically conductive tubular wall 22 of the tubular shaft 20 is also held, so that, at this point, there is an electrically conductive connection between the passive electrode 72 and the electrically conductive tubular wall 22 of the tubular shaft 20, which forms the passive conductor. In the radial direction toward the outside, the shaft 20 can also be wrapped, if desired, with electrical insulation, so that the electrically conductive tubular wall 22 of the tubular shaft 20 does not form the surface of the tubular shaft 20 in this direction.

In the area of the distal end of the electrically conductive tubular wall 22 of the shaft 20, an electrical contact is created to the distal end of the metallic wire 30, which at least has sections that are arranged moveable in the interior of the shaft 20. Here, the metallic wire 30 can be wrapped, apart from its contact sections, with electrical insulation 31, which can be formed, for example, by a PTFE sleeve, so that electrical insulation in the radial direction relative to the electrically conductive tubular wall 22 of the tubular shaft 20 is guaranteed in the sections of the metallic wire 30 running in the interior of the tubular shaft 20. The proximal end of the metallic wire 30 is connected to a contact element 32.

Here, one bearing section 32a of the contact element 32 can be held together with the proximal end section of the metallic wire 30 in the body 42 of a slide 40, while a contact section 32b of the contact element 32 projects out of the body 42 of the slide 40. The slide 40 is connected with a connecting section 43 to a control element 41 arranged outside of the housing, wherein the connecting section 43 is guided in a slot of the housing running parallel to the center axis of the tubular shaft 20.

Accordingly, the control element 41 can be moved in the direction parallel to the center axis of the tubular shaft 20, which then leads to a corresponding shifting of the body 42 of the slide 40. If this moves in the distal direction, the metallic wire 30 held in the body 42 of the slide is moved in the same direction, whereby its distal end section is further extended out from the interior of the tubular shaft 20 and forms or increases the size of the loop 33. If the slide 40 moves in the proximal direction, the body 42 moves in this direction and consequently retracts the loop 33.

To close the current circuit, the contact section 32*b*, which moves with the movement of the slide 40 or its body in the axial direction, must be in electrically conductive connection to the active electrode 71. To enable this, the distal section 71*a* of the active electrode 71 extends in the direction toward the center axis of the tubular shaft 20 and ends at a level at which the contact section 32*b* is located, so that, in the distal end position of the slide 40, the electrical contact is established between the distal section 71*a* of the active electrode 71 and the contact section 32*b* and is lost when it moves in the proximal direction. Accordingly, the contact section 32*b* and the distal section 71*a* of the active electrode 71 form the contacts of a switch and the slide 40 forms the control element with which these contacts of the switch can be brought into contact with each other and then separated from each other again.

In the shown embodiment, the electrical contact is established such that there is a first contact surface 32*c* of the contact section 32*b*, which runs essentially parallel to the distal section of the active electrode 71, so that an electrical surface area contact is produced between the first contact surface 32*c* and the distal section 71*a* of the active electrode 71, which is preferably further improved by a slight spring tension of the active electrode 71.

The contact section 32*b* has a second contact surface 32*d*, which connects in the proximal direction to the first contact surface 32*c* and runs in the space so that its distance to the center axis of the tubular shaft 20 decreases in the proximal direction. In the illustration of FIG. 3, the second contact surface 32*d* contacts a surface area spring element 65, which is mounted in the housing wall 61, for example, injection molded there. Preferably, the surface area spring element 65, as shown in FIGS. 3 and 4, is mounted in a slightly tilted position, so that its distal edge has a smaller distance from the center axis of the tubular shaft 20 than its proximal edge, wherein its slope in the direction from the proximal to distal edge is preferably less than that of the first contact surface 32*c*, as can be seen especially in FIG. 4.

The slide 40 and thus also the contact section 32*b* of the contact element 32 mounted in the body 42 of the slide 40 is fixed in its end position that corresponds to the closed position of the switch, and is preferably also pressed against the distal section 71*a* of the active electrode 71, as shown in FIG. 3.

Due to the inclined arrangement of the second contact surface 32*c*, however, if the user applies a corresponding force via the control element 41 of the slide 40, this fixing can be overcome and the surface area spring element 65 can be pressed away from the center axis of the tubular shaft 20, so that the electrical contact between the contact section 32*b* and the distal section 71*a* of the active electrode 71 is broken and the current flow is interrupted. In this way, the second contact surface 32*d* initially slides over the distal edge of the surface area spring element 65 and presses this downward to the connecting line between the first contact surface 32*c* and second contact surface 32*d*, which is formed by the line of the contact section 32*b*, which is farthest removed from the center axis of the tubular shaft 20, reaching the surface area spring element 65. From this point on, the surface area spring element 65 supports the movement of the slide 49 in the proximal direction until it reaches its proximal stop.

In one preferred method for producing such a surgical instrument 10, the housing forming the handle 60 is provided in two half shells 60*a*, of which at least one can have the guiding elements 62 mentioned above, the rib 64, and the surface area spring element 65. These components, however, can also be assembled from subsections present on both half shells 60*a*.

The metallic wire 30 wrapped with the electrical insulation 31 is connected to the contact element 32 and the slide 40 injection molded with the body 42, connecting piece 43, and control element 41, preferably with plastic.

The active electrode 71 and the passive electrode 72 are formed connected to the contacts of the connection 70 and the connection itself is produced by injection molding, preferably with plastic.

The electrically conductive tubular wall 22 of the tubular shaft 20 is connected to the flange 73. Then the metallic wire wrapped with the electrical insulation 31 is fed into the interior of the tube, pushed to the distal end, and the contact with the electrically conductive tubular wall 22 is created there. Furthermore, the passive electrode 72 is inserted into a slot in the flange 73. For creating the electrode assembly, the connection 70 can be connected to connecting cables and secured with bend protection.

The electrode assembly can then be placed in one of the half shells, wherein especially the active electrode 71 and the passive electrode 72 are pushed into the guiding elements 62, in order to hold them. Then the other half shell 60*a* of the housing, which forms the handle 60, is pressed on, and in this way the housing is assembled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

LIST OF REFERENCE SYMBOLS

10 Surgical instrument
20 Tubular shaft
22 Tubular wall
30 Metallic wire
31 Insulation
32 Contact element
32*a* Bearing section
32*b* Contact section
32*c* First contact surface
32*d* Second contact surface
33 Loop
40 Slide
41 Control element
42 Body
43 Connecting section
60 Handle
60*a* Half shell
61 Housing wall
62 Guiding element
64 Rib

65 Spring element
70 Electrical connection
71 Active electrode
71*a* Distal section
72 Passive electrode
73 Flange

The invention claimed is:

1. A surgical instrument comprising:

a handle and a tubular shaft with an interior and a wall made from an electrically conductive material, wherein a metallic wire is arranged in the interior of the tubular shaft, the metallic wire configured to be moved by actuation of a control element so that a loop can be extended out of a distal end of the tubular shaft, and with a switch, wherein the metallic wire can be energized by the actuation of the switch, the control element and the switch are coupled with each other so that the metallic wire is energized only in one or more defined positions of the metallic wire, wherein the control element is part of a slide and the slide has a body in which an end section of the metallic wire is held and fixed, wherein a bearing section of a contact element, which is connected in an electrically conductive way to the metallic wire, is housed in the body of the slide and a contact section of the contact element projects out from the body, so that the slide forms a control element of the switch and the contact section of the contact element forms a first switch contact of the switch.

2. The surgical instrument according to claim 1, wherein the metallic wire is energized only in a position of the control element in which the loop is extended.

3. The surgical instrument according to claim 1, wherein the control element is held in a position in which the metallic wire is energized so that a holding force must be overcome to move the control element into a different position.

4. The surgical instrument according to claim 1, wherein the control element is held in a position in which the loop is retracted as small as possible or completely into the interior of the tubular shaft so that a holding force must be overcome to move the control element into a different position.

5. The surgical instrument according to claim 3, characterized in that the holding force is provided by a spring element.

6. The surgical instrument according to claim 1, characterized in that a second switch contact of the switch is formed by a distal end section of an electrode that is constructed as a sheet and is connected to an electrical connection of the surgical instrument.

7. The surgical instrument according to claim 6, characterized in that a distance of the distal end section of the electrode constructed as a sheet from a center axis of the tubular shaft decreases in a distal direction and the contact section of the contact element has a first contact surface which runs essentially parallel to the distal end section of the electrode constructed as a sheet, so that by moving the slide in the distal direction, a surface area contact can be created between the first contact surface and the distal end section of the electrode constructed as a sheet.

8. The surgical instrument according to claim 1, characterized in that the contact section of the contact element has a second contact surface, whose distance from a center axis of the tubular shaft decreases in a proximal direction and for a closed switch and completed extended loop, a spring element contacts the second contact surface and the spring element is further tensioned by the second contact surface when the slide moves in the proximal direction.

\* \* \* \* \*